US012642659B2

(12) United States Patent　　(10) Patent No.: US 12,642,659 B2
Naylor et al.　　(45) Date of Patent: Jun. 2, 2026

(54) SURGICAL INSTRUMENTS AND METHODS

(71) Applicant: DEPUY IRELAND UNLIMITED COMPANY, Ringaskiddy (IE)

(72) Inventors: Jason Naylor, Leeds (GB); Stephen Robinson, Leeds (GB); Charlie Weston, Leeds (GB); Caroline Wither, Leeds (GB)

(73) Assignee: DEPUY IRELAND UNLIMITED COMPANY, LOUGHBEG INDUSTRIAL ESTATE, Ringaskiddy (IE)

( * ) Notice: Subject to any disclaimer, the term of this patent is extended or adjusted under 35 U.S.C. 154(b) by 1023 days.

(21) Appl. No.: 17/785,659

(22) PCT Filed: Dec. 24, 2020

(86) PCT No.: PCT/EP2020/087877
　　§ 371 (c)(1),
　　(2) Date: Jun. 15, 2022

(87) PCT Pub. No.: WO2021/130372
　　PCT Pub. Date: Jul. 1, 2021

(65) Prior Publication Data
　　US 2023/0056410 A1　　Feb. 23, 2023

(30) Foreign Application Priority Data
　　Dec. 24, 2019　　(GB) ..................................... 1919271

(51) Int. Cl.
　　*A61F 2/28*　　　　(2006.01)
　　*A61F 2/30*　　　　(2006.01)
　　(Continued)

(52) U.S. Cl.
　　CPC ........ *A61F 2/30723* (2013.01); *A61F 2/4614* (2013.01); *A61F 2/4684* (2013.01); *A61F 2002/30617* (2013.01)

(58) Field of Classification Search
　　None
　　See application file for complete search history.

(56) References Cited

U.S. PATENT DOCUMENTS

| 3,866,248 A | * | 2/1975 | Kummer ............. A61F 2/30723 |
| | | | 606/92 |
| 4,245,359 A | | 1/1981 | Stuhmer |

(Continued)

FOREIGN PATENT DOCUMENTS

| AU | 758896 B2 | * | 4/2003 | ............. A61F 2/367 |
| CN | 1169850 A | | 1/1998 | |

(Continued)

OTHER PUBLICATIONS

PCT/EP2020/087877—ISR dated May 4, 2021.
(Continued)

*Primary Examiner* — Ann Hu

(57) ABSTRACT

A cement restrictor inserter instrument (130) comprises an inserter (131) having a handle (132) at a proximal end, a cement restrictor attachment formation (137) at a distal end for releasably attaching a cement restrictor (150), a shaft (136) extending from the proximal end to the distal end and a stop (138) on the shaft and between the proximal end and the distal end; and a body (140) having a shape corresponding to the shape of an orthopaedic prosthetic implant, a spacer (142), a visible depth guide feature (190) and a releasable attachment mechanism by which the body is releasably attachable to the shaft, and wherein the spacer is configured to position the visible depth guide feature at a fixed position relative to the inserter when the spacer abuts the stop corresponding to a target cement restrictor position
(Continued)

when the visible depth guide feature is aligned with a feature of a bone of a patient in which the cement restrictor is to be inserted.

13 Claims, 9 Drawing Sheets

(51) Int. Cl.
    *A61F 2/32*          (2006.01)
    *A61F 2/40*          (2006.01)
    *A61F 2/46*          (2006.01)

(56)                References Cited

U.S. PATENT DOCUMENTS

| | | | | | |
|---|---|---|---|---|---|
| 5,002,580 | A * | 3/1991 | Noble | ................. | A61F 2/30724 623/23.23 |
| 5,047,035 | A * | 9/1991 | Mikhail | ............. | A61B 17/8847 606/92 |
| 5,062,854 | A * | 11/1991 | Noble | ................. | A61F 2/30724 128/898 |
| 5,078,746 | A * | 1/1992 | Garner | ................ | A61F 2/30723 606/95 |
| 5,833,932 | A | 11/1998 | Schmelz | | |
| 5,888,207 | A | 3/1999 | Nieder | | |
| 5,972,034 | A * | 10/1999 | Hofmann | ............ | A61F 2/30723 606/95 |
| 5,997,580 | A * | 12/1999 | Mastrorio | ............. | A61F 2/4614 606/95 |
| 5,997,581 | A * | 12/1999 | Khalili | ................ | A61F 2/30724 606/92 |
| 6,267,785 | B1 * | 7/2001 | Masini | ................ | A61F 2/30724 623/23.22 |
| 7,229,478 | B2 * | 6/2007 | Masini | ................ | A61F 2/30724 623/23.19 |
| 10,463,402 | B2 * | 11/2019 | Biester | ............... | A61B 17/7007 |
| 10,888,363 | B2 * | 1/2021 | Greenhalgh | ....... | A61B 17/7098 |
| 11,123,085 | B2 * | 9/2021 | Servidio | ............ | A61B 17/1764 |

| | | | | | |
|---|---|---|---|---|---|
| 2002/0065518 | A1 * | 5/2002 | Naybour | ............... | A61F 2/4601 606/86 R |
| 2003/0163205 | A1 * | 8/2003 | Lawson | .............. | A61F 2/30723 606/95 |
| 2004/0015238 | A1 | 1/2004 | Buehler et al. | | |
| 2004/0162619 | A1 * | 8/2004 | Blaylock | ............. | A61F 2/30734 606/88 |
| 2005/0203508 | A1 * | 9/2005 | Thelen | ............... | A61B 17/1642 606/53 |
| 2005/0203537 | A1 | 9/2005 | Wiley et al. | | |
| 2006/0015188 | A1 * | 1/2006 | Grimes | ................. | A61F 2/3601 623/23.22 |
| 2014/0128987 | A1 * | 5/2014 | Kelley | .............. | A61B 17/1659 623/22.12 |
| 2014/0276857 | A1 | 9/2014 | Major | | |
| 2019/0117412 | A1 | 4/2019 | Zimmerman et al. | | |

FOREIGN PATENT DOCUMENTS

| | | | | | |
|---|---|---|---|---|---|
| EP | 0178174 | A2 * | 4/1986 | ........ | A61F 2/30723 |
| EP | 0379785 | A1 | 8/1990 | | |
| EP | 0626155 | A1 | 11/1994 | | |
| EP | 0995410 | A2 * | 4/2000 | .......... | A61F 2/4601 |
| EP | 1393695 | A1 * | 3/2004 | ........ | A61F 2/30723 |
| EP | 2704648 | B1 | 6/2016 | | |
| EP | 1208821 | A2 | 5/2020 | | |
| GB | 2253564 | A * | 9/1992 | ........ | A61F 2/30723 |
| GB | 2323535 | A | 9/1998 | | |
| GB | 2344052 | A * | 5/2000 | ........ | A61B 17/8811 |
| GB | 2376894 | A * | 12/2002 | ........ | A61F 2/30723 |
| WO | WO-9301773 | A1 * | 2/1993 | .......... | A61F 2/4614 |
| WO | WO-03065941 | A1 * | 8/2003 | .......... | A61F 2/4614 |

OTHER PUBLICATIONS

Great Britain Search report received for GB Application No. 1919271. 5, mailed on Jun. 23, 2020, 1 page.
Chinese Notice of Allowance for Corresponding Chinese Application No. 202080090018.9, Dated Jun. 10, 2025, 4 Pages.

* cited by examiner

DETAIL N
SCALE 2:1

SECTION L - L

Figure 6:
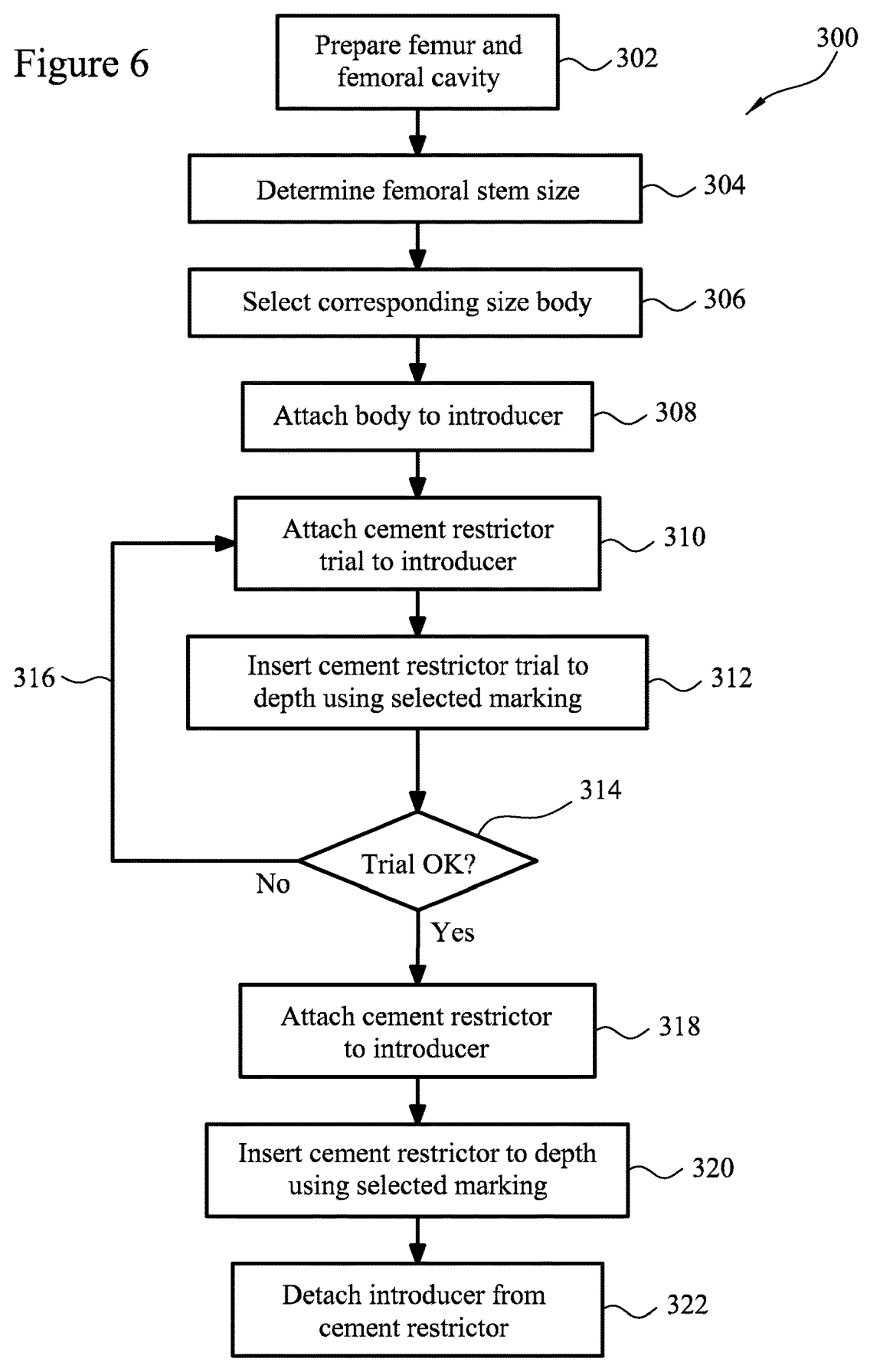

```
┌─────────────────────────┐
│   Prepare femur and     │── 302
│    femoral cavity       │
└─────────────────────────┘
            │
            ▼
┌─────────────────────────┐
│ Determine femoral stem  │── 304
│          size           │
└─────────────────────────┘
            │
            ▼
┌─────────────────────────┐
│ Select corresponding    │── 306
│       size body         │
└─────────────────────────┘
            │
            ▼
┌─────────────────────────┐
│  Attach body to         │── 308
│    introducer           │
└─────────────────────────┘
            │
            ▼
┌─────────────────────────┐
│  Attach cement          │── 310
│  restrictor trial to    │
│     introducer          │
└─────────────────────────┘
            │
            ▼
┌─────────────────────────┐
│ Insert cement restrictor│── 312
│ trial to depth using    │
│   selected marking      │
└─────────────────────────┘
            │
            ▼
         ◇ Trial OK? ◇ ── 314
```

316

No

Yes

```
┌─────────────────────────┐
│  Attach cement          │── 318
│  restrictor             │
│    to introducer        │
└─────────────────────────┘
            │
            ▼
┌─────────────────────────┐
│ Insert cement restrictor│── 320
│ to depth using selected │
│       marking           │
└─────────────────────────┘
            │
            ▼
┌─────────────────────────┐
│  Detach introducer from │── 322
│    cement restrictor    │
└─────────────────────────┘
```

SURGICAL INSTRUMENTS AND METHODS

CROSS-REFERENCE TO RELATED APPLICATIONS

This application is a National Stage Application filed Under 35 U.S.C. § 371 of International Application No. PCT/EP2020/087877 filed Dec. 24, 2020, which claims priority to GB1919271.5 filed Dec. 24, 2019, which are hereby incorporated by reference in their entireties.

The present disclosure relates to surgical instruments and methods and in particular, but not exclusively, to surgical instruments and methods for placing cement restrictors during orthopaedic procedures.

Some orthopaedics procedures use cemented implants in which cement is used to help secure the prosthetic orthopaedic implant in the bone of the patient. Often, as part of the surgical procedure, a cavity is formed in the bone to receive the prosthetic implant. Cement is then introduced into the cavity and then the prosthetic implant is inserted.

In some cases, a cement restrictor may be inserted in the cavity before the cement is introduced. The cement restrictor may serve various purposes. The cement restrictor may provide a solid foundation against which cement may be pressurised in order to ensure god introduction of cement into the cavity. Additionally, or alternatively, the cement restrictor may prevent, or reduce the amount of, cement passing beyond it and further into the prepared cavity. An excess of cement in the cavity may introduce difficulties should revision surgery be required later on, for example, requiring the excess cement to be removed from the cavity during revision surgery.

Irrespective of the reason for using the cement restrictor, there is generally a preferred position or depth within the cavity at which the cement restrictor should be placed. This preferred position or depth may be related to the position of the prosthetic implant in order to try and ensure that there is a preferred amount of cement between the cement restrictor and the prosthetic implant. Too much cement between the cement restrictor and implant gives rise to the same potential difficulties for revision surgery mentioned above and too little may reduce the ability for the prosthetic implant to settle properly after insertion and/or properly to fix the implant within the cavity.

Hence, correctly positioning the cement restrictor is generally desirable. However, the correct position of the cement restrictor may be a function of the size and/or type of implant being used. Also, the surgeon has no easy way of visualising the position of the cement restrictor during insertion as the cement restrictor will be hidden from view within some cavity.

Introducers for cement restrictors have been provided with various markings thereon to provide some guidance to the surgeon as to the depth to which the cement restrictor has been inserted. However these marking may be difficult to see and/or read during surgery. Also, the anatomical feature against which these markings should be aligned may be hard to visualise at the surgical site and/or ill defined. Also, there may be no clear relationship between the various markings and the insertion depth that the surgeon is currently trying to achieve for the intended prosthetic implant. It may be difficult for the surgeon reliably to recall which of the multiple markings they should currently be using. This issue is exacerbated for more sophisticated implant systems in which the appropriate position for a cement restrictor varies in a more complex way with the different sizes of implants that may be available.

Hence, instruments and methods which may facilitate the ease and/or reliability with which cement restrictors may be positioned would be beneficial.

According to a first aspect of the present disclosure there is provided a cement restrictor inserter instrument comprising: an inserter having a handle at a proximal end, a cement restrictor attachment formation at a distal end for releasably attaching a cement restrictor, a shaft extending from the proximal end to the distal end and a stop on the shaft and between the proximal end and the distal end; and a body having a shape corresponding to the shape of an orthopaedic prosthetic implant, a spacer, a visible depth guide feature and a releasable attachment mechanism by which the body is releasably attachable to the rod, and wherein the spacer is configured to position the visible depth guide feature at a fixed position relative to the inserter when the spacer abuts the stop corresponding to a target cement restrictor position when the visible depth guide feature is aligned with a feature of a bone of a patient in which the cement restrictor is to be inserted.

The releasable attachment mechanism may include a push fit or snap fit mechanism.

The stop may include an attachment formation and the releasable attachment mechanism may interact with the attachment formation.

The releasable attachment formation may include a C-clip or circlip and a groove arranged to receive the C-clip or circlip. The C-clip or circlip may be within a part of the stop and/or the releasable attachment mechanism of the body may include the groove.

The body may define an open channel or a closed channel and configured to accept the shaft. The channel may extend along a longitudinal axis of the body and/or extend along an axis parallel to a longitudinal axis of the shaft.

The releasable attachment mechanism may be a rotary releasable attachment mechanism. The releasable attachment mechanism may permit rotation of the shaft relative to the body.

The cement restrictor attachment formation may comprise a push fit formation.

The cement restrictor attachment formation may comprise a rotary attachment mechanism. The rotary attachment mechanism may be a screw thread.

The visible depth guide feature may comprise a surface or an edge of a part of the body.

The visible depth guide feature may comprise a marking on a surface of a part of the body.

The visible depth guide feature may comprise a plurality of markings on the surface of the part of the body. Each of the plurality of markings may correspond to a different position, or depth of insertion, of the orthopaedic prosthetic implant relative to the bone of the patient.

The orthopaedic prosthetic implant may be a humeral stem, a shoulder component, a femoral stem, a femoral component of a knee or a tibial component.

The body may have a size corresponding to the size of the orthopaedic prosthetic implant. The body may have a size with dimensions corresponding to the size of the orthopaedic prosthetic implant to within 1 mm, 2 mm, 3 mm, 4 mm or 5 mm.

The body may be mounted on the inserter with the spacer abutting or engaging or mating with the stop.

A further aspect of the disclosure provides a kit of surgical instrument parts comprising: the cement restrictor inserter instrument of the first aspect; and a further body having a shape corresponding to the shape of the orthopaedic prosthetic implant, a further spacer, a further visible depth guide feature and a further releasable attachment mechanism by which the further body is releasably attachable to the shaft. The further body may have a different size to the body. The further body may have a different length and/or a different width. The further body may be larger or smaller than the body. A plurality of further bodies may be provided and each body may have a different size and/or the same shape.

The further body may have a different size to the body and may correspond to the shape of a different size of the orthopaedic prosthetic implant. The further spacer may have a different size to the spacer and may be configured to position the further visible depth guide feature at a different fixed position relative to the inserter when the further spacer abuts the stop corresponding to the target cement restrictor position when the further visible depth guide feature is aligned with the feature of the bone of the patient in which the cement restrictor is to be inserted.

A further aspect of the disclosure provides a method of inserting a cement restrictor in a cavity in a bone of a patient, the method comprising: selecting a body having a shape corresponding to the shape of an orthopaedic prosthetic implant to be implanted in a cavity in a bone of a patient, wherein the body includes a visible depth guide feature; releasably attaching the body to a shaft of a cement restrictor inserter at a pre-determined position; attaching a cement restrictor to a distal end of the shaft of the cement restrictor inserter; inserting the cement restrictor inserter with the body mounted thereon into the cavity to a depth determined by the visible depth guide feature being aligned with a feature of the bone of the patient.

The method may further comprise rotating the shaft of the cement restrictor inserter relative to the body to detach the cement restrictor from the distal end of the rod; and withdrawing the cement restrictor inserter from the cavity.

Selecting the body may further comprise selecting the body having a size corresponding to the size of the orthopaedic implant to be implanted in the cavity of the bone of the patient.

The method may further comprise: determining the size of the orthopaedic implant to be implanted is based on a final trial component or a final broach or a final reamer or a final cutting instrument, before selecting the body.

The method may further comprise attaching a cement restrictor trial to the distal end of the shaft and inserting the cement restrictor inserter into the cavity to trial a size for the cement restrictor, after attaching the body and before attaching the cement restrictor.

The feature of the bone of the patient may be an anatomical feature of the bone of the patient.

The feature of the bone of the patient may be a resected surface or edge or rim of the bone of the patient.

The visual depth guide may be a surface or an edge of the body.

The visual depth guide feature may be a marking on a surface of the body.

The visual depth guide feature may comprise a plurality of markings on a surface of the body. Each marking may correspond to a different position of the orthopaedic prosthetic implant relative to the bone of the patient, for example a depth of insertion. The method may further comprise using the marking corresponding to a selected one of the different positions to determine the depth to which the cement restrictor inserter is inserted.

The prosthetic orthopaedic implant may be a femoral stem. The feature of the bone of the patient may be a proximal resection of the femur or a neck resection of the femur.

The prosthetic orthopaedic implant may be a tibial component. The feature of the bone of the patient may be a proximal resection of the tibia.

The prosthetic orthopaedic implant may be a humeral stem. The feature of the bone of the patient may be a proximal resection of the humerus or a rim of a cavity reamed in the proximal humerus.

Embodiments will now be described in detail, by way of example only, and with reference to the accompanying drawings, in which:

FIG. 6 shows a flow chart illustrating a method of use of the cement restrictor inserter instrument according to an aspect of the disclosure;

Figures 8A, 8B, 9A, 9B:
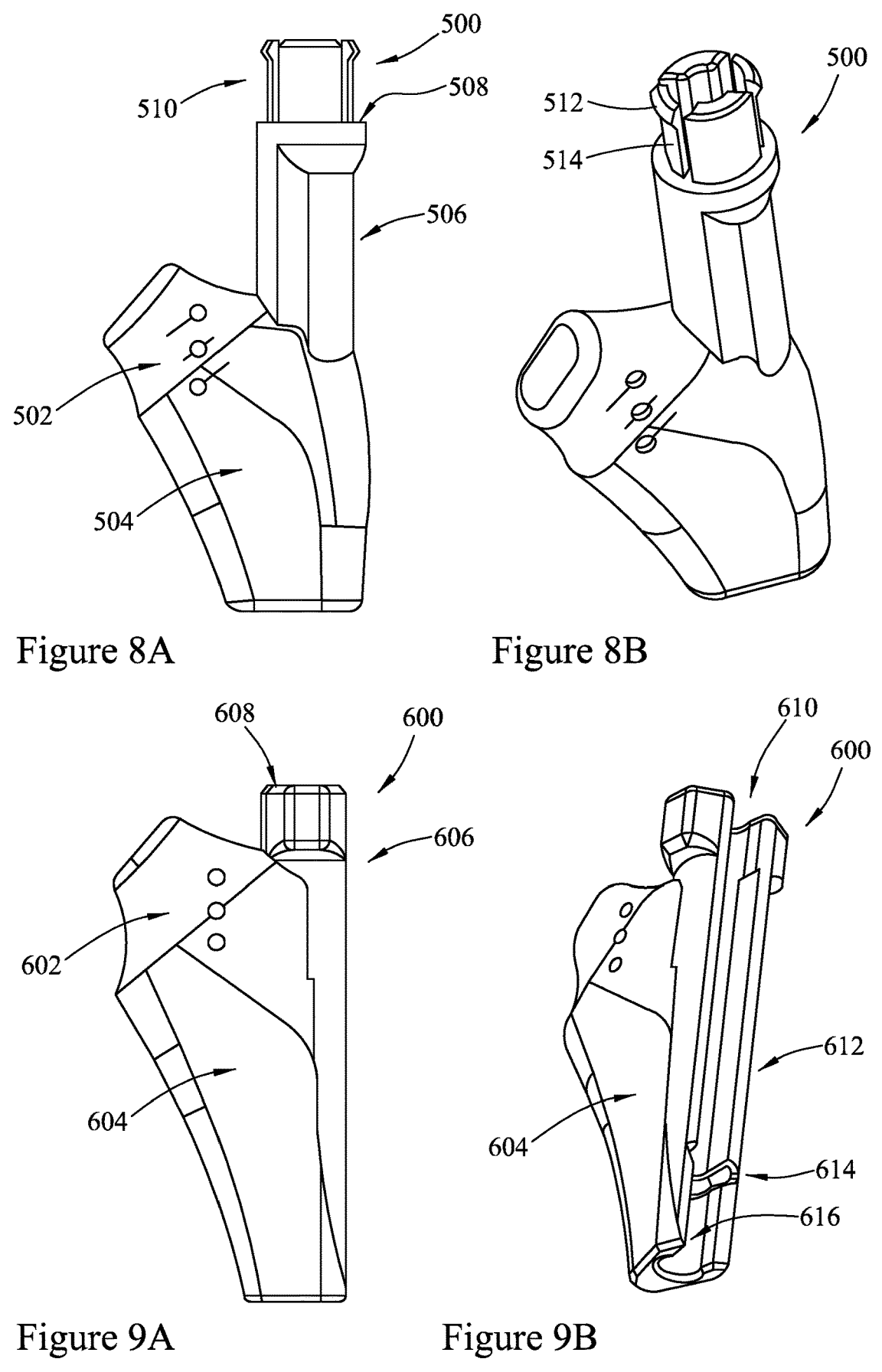
Figure 10A:
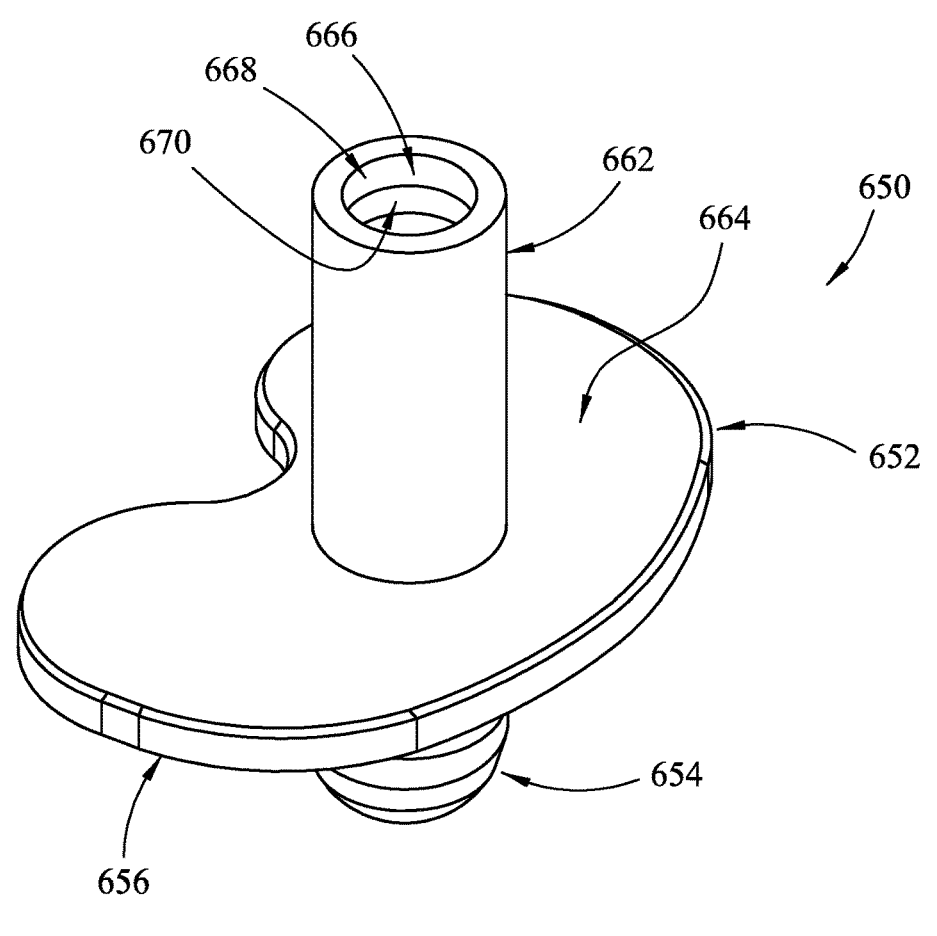
Figure 10B:
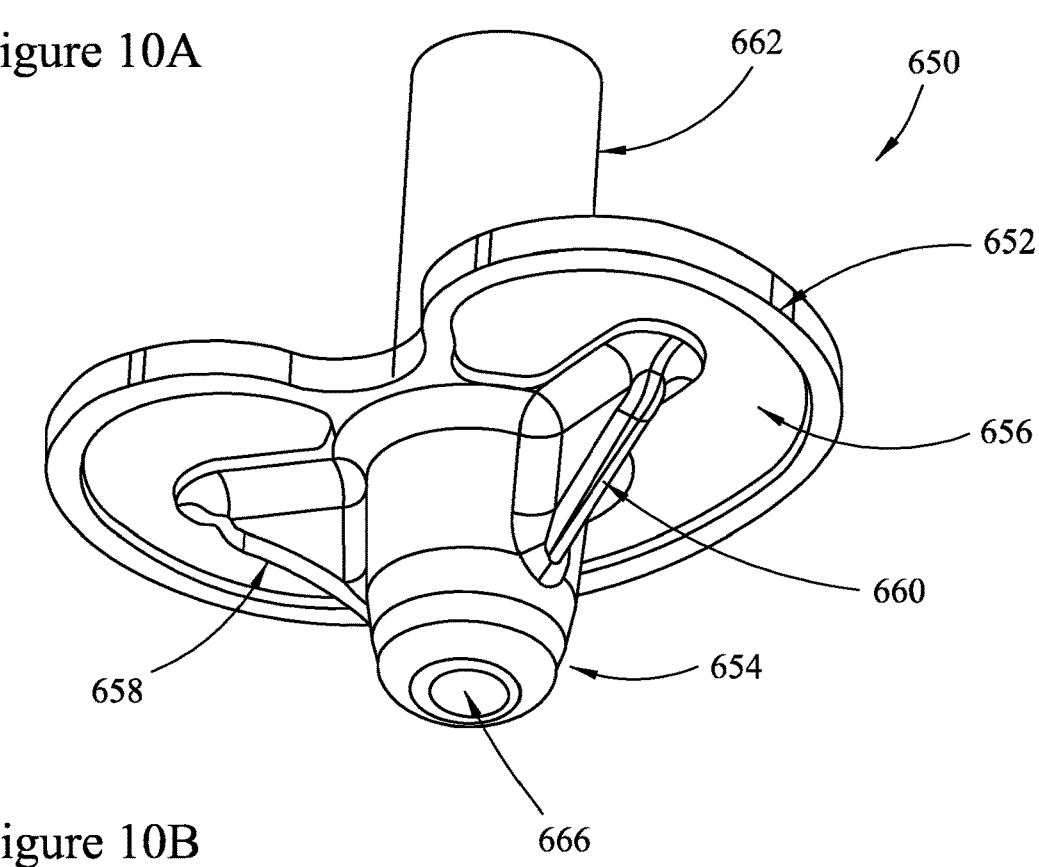
Figures 11, 12:
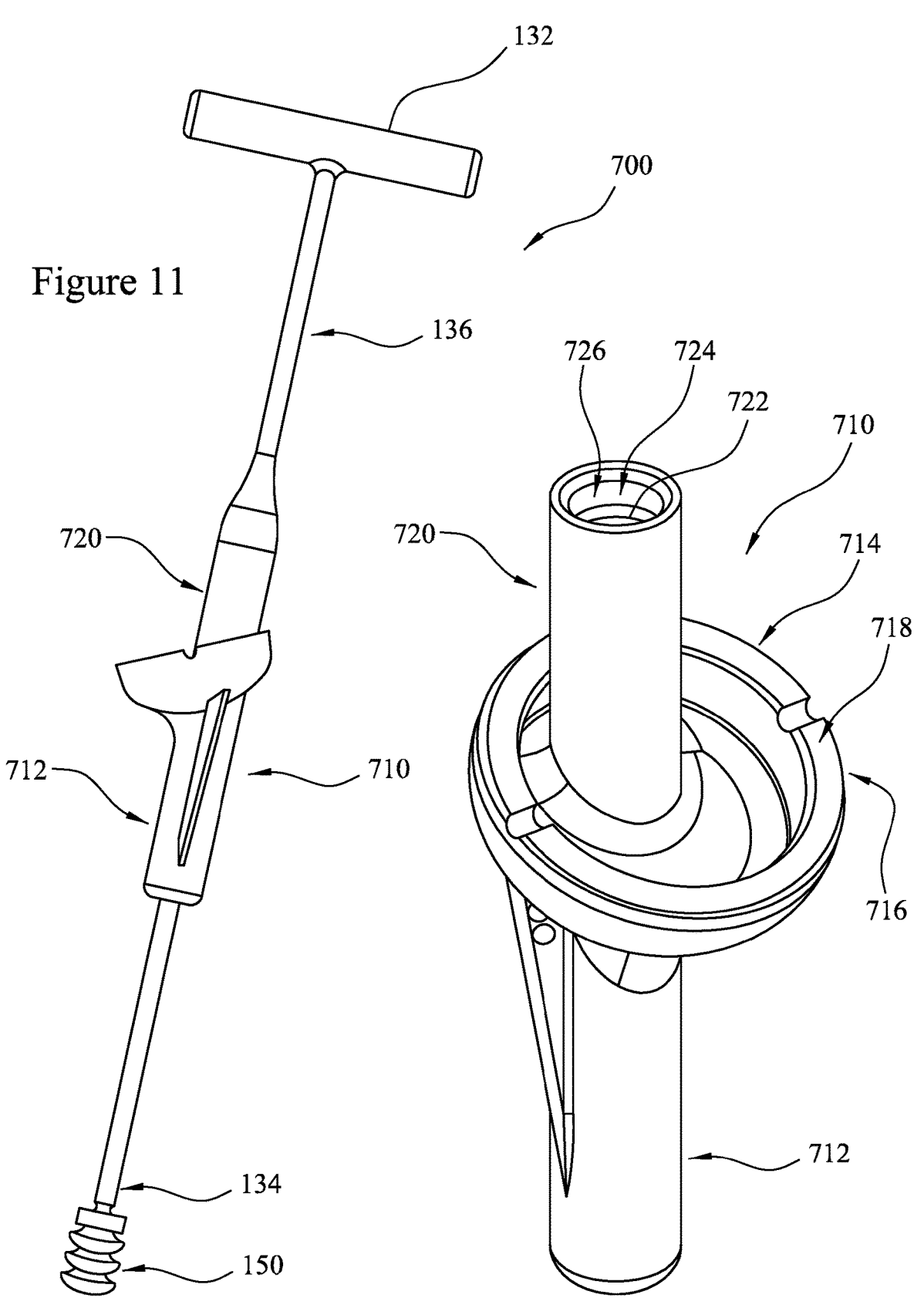

FIGS. 8A and 8B respectively show a side elevation and a 3D view of a second embodiment of the body part;

FIGS. 9A and 9B respectively show a side elevation and a 3D view of a third embodiment of the body part;

FIGS. 10A and 10B respectively show 3D views from above and below of a fourth embodiment of a body part that may be used with the inserter of FIG. 3 to provide a further embodiment of the instrument;

FIG. 11 shows a 3D view of a cement restrictor inserter instrument according to a second embodiment; and FIG. 12 shows a 3D view of a fifth embodiment of a body part used in the instrument shown in FIG. 11.

In the Figures of drawings, the same reference numerals are used to refer to refer to like parts unless indicated otherwise.

Figure 1:
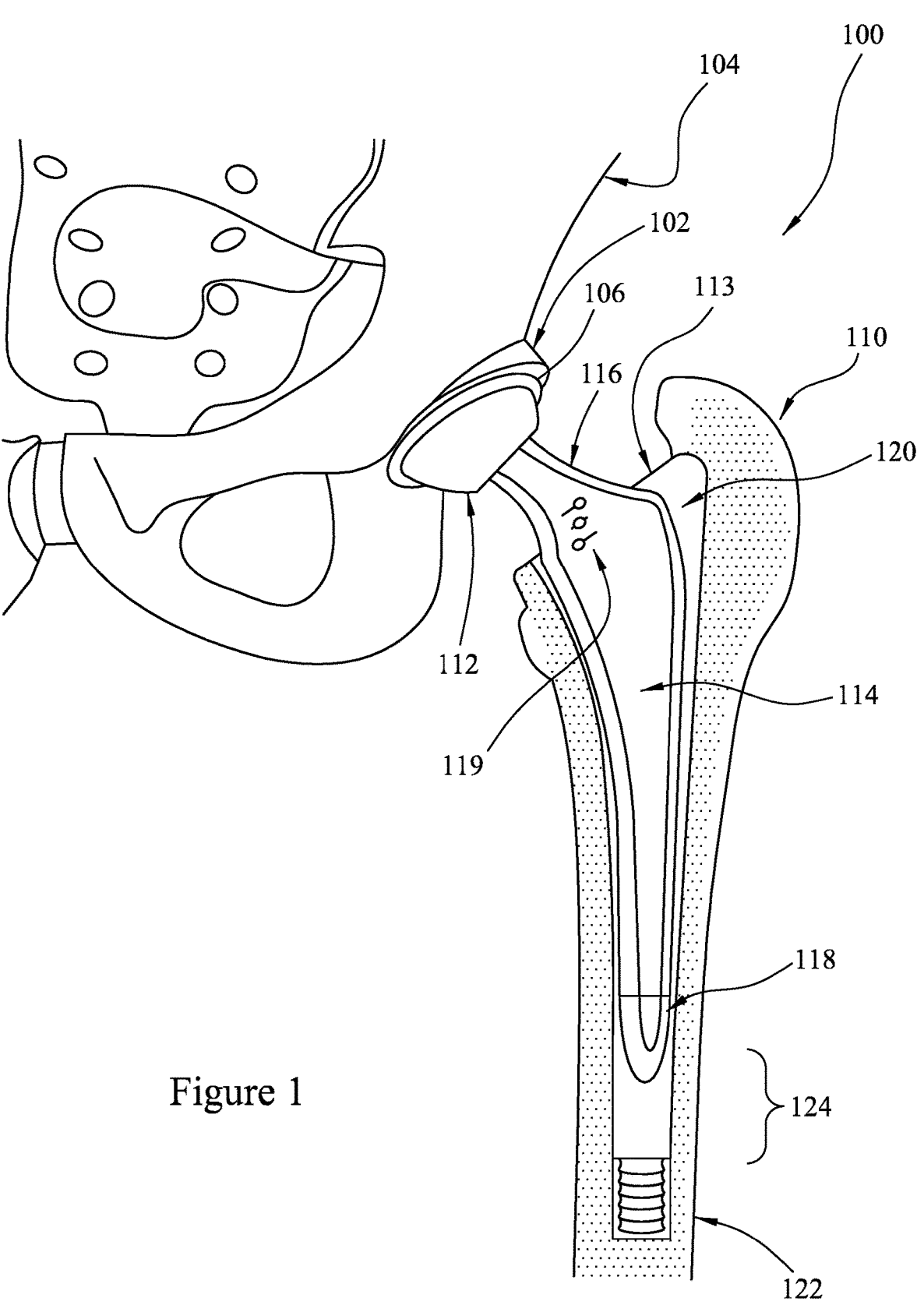
FIG. 1 shows a view of a prosthetic hip joint illustrating the preferred relative positioning of a prosthetic stem implant and a cement restrictor within a femur of a patient.

With reference to FIG. 1, there is shown a view of a hip joint of a patient 100 which has undergone a total hip replacement surgical procedure. The prosthetic components include an acetabular cup 102 implanted in the prepared acetabulum of the pelvis 104 of the patient. As illustrated in FIG. 1, the acetabular cup 102 includes a liner 106 providing an articulating surface. A cross section view of the proximal part of the femur 110 of the patient is also shown. The femoral part of a prosthesis includes a femoral head 112 mounted on a femoral stem 114 via a neck 116. A distal end of the femoral stem 114 includes a centraliser 118. The femoral stem 114 is located within a cement mantel 120 within an intramedullary cavity of the femur. Toward the distal end of the intramedullary cavity there is provided a cement restrictor 122. As illustrated in FIG. 1, there is a gap between the distal most part of the femur (stabiliser 118) and the cement restrictor 122 of side 124 which is preferably approximately 10-20 mm.

Preferably, the cement mantel 120 has a thickness of a few millimetres, e.g. approximately 2 mm, around the stem 114 which is generally centrally located within the intramedullary cavity of the femur. Also, preferably, the distance between a distalmost portion of the stem and the cement restrictor 124 is sufficient to allow the stem 114 to settle within the cement. However, it is not so great that excess cement is present within the intramedullary cavity, for example, to avoid difficulties in removing that cement, should revision surgery subsequently be required. In practice, the distance 124 is preferably approximately 20 mm.

The use of a cement restrictors is generally understood by a person of ordinary skill in the art, and cement restrictors can be used in other orthopaedic procedures in which some prosthetic component is cemented in place within a cavity of a patient's bone. As briefly discussed above, preferably, there is some finite distance between the cement restrictor and distal most part of the prosthetic implant component. However, the difficulty arises in trying to ensure that the cement restrictor 122 is placed at a depth within the cavity likely to give rise to the preferred separation 124 between the end of the prosthetic component and the cement restrictor. This is not something that can be achieved visually as the cement restrictor 122 is hidden from view when inserted into the cavity prior to cementation.

Figure 2:
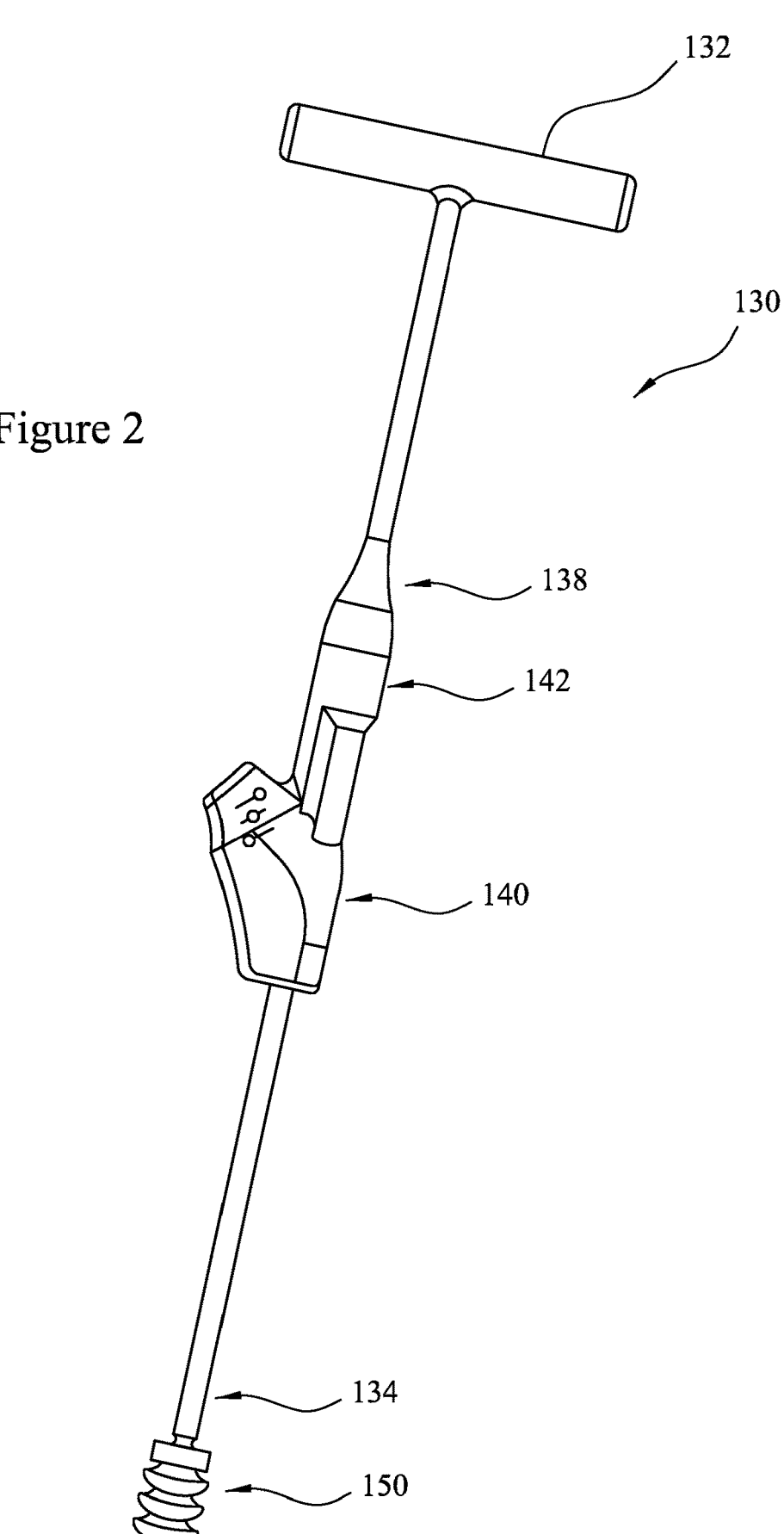
FIG. 2 shows a 3D view of a cement restrictor inserter instrument according to a first embodiment.

FIG. 2 shows a side view of a cement restrictor inserter instrument 130 according to a first embodiment and having a cement restrictor 150 attached to a distal end thereof. The cement restrictor inserter instrument 130 has a handle 132 at a proximal end and an attachment formation at a distal end 134 (not visible in FIG. 2) via which the cement restrictor 150 can releasably attach to the inserter instrument 130. A shaft 136 extends from the handle 132 to the distal end 134. A stop 138 is provided on the shaft between the proximal and distal ends. A body 140 is provided on the shaft 136. The position of the body 140 along the shaft 136 is controlled by stop 138 abutting a spacer part 142 of body 140.

Figure 3:
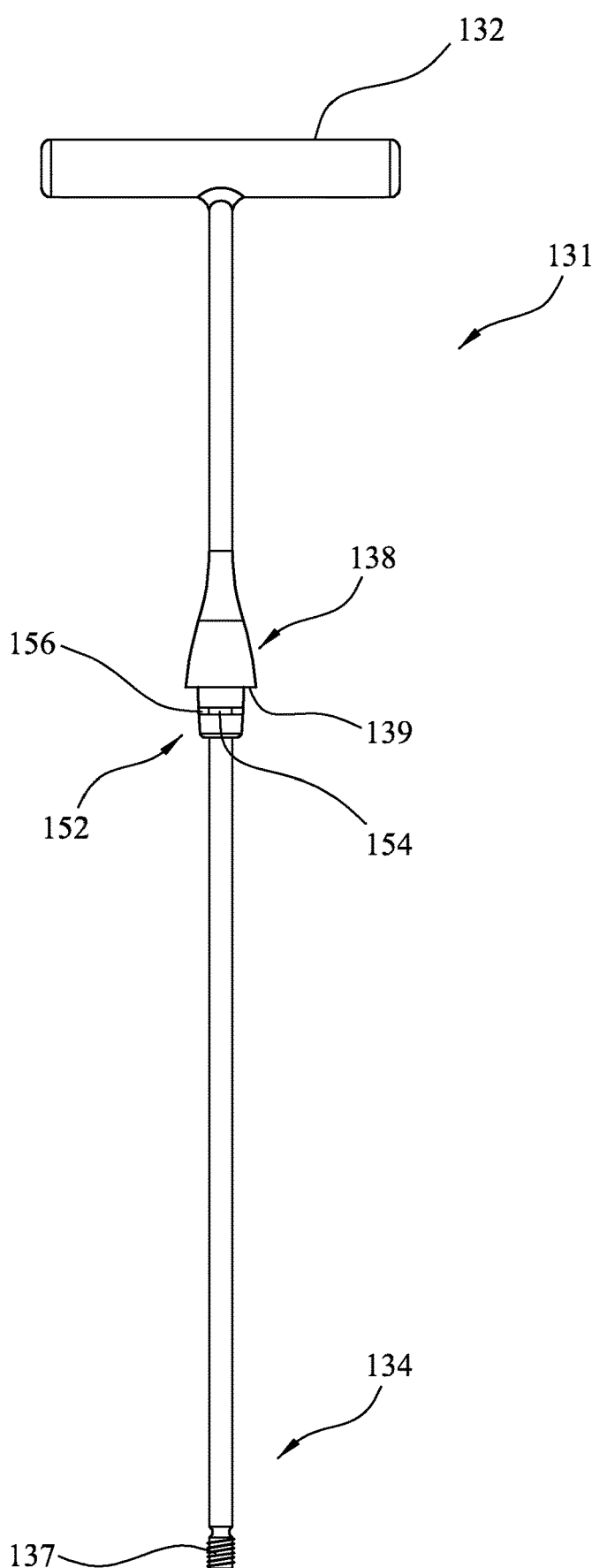
FIG. 3 shows a side elevation of a cement restrictor inserter part of the instrument shown in FIG. 2.

FIG. 3 shows a side elevation of the cement restrictor inserter 131 being part of the overall instrument 130, omitting the body 140. Hence, the overall instrument 130 may be considered an assembly of the body 140 and the inserter 131. As illustrated in FIG. 3, the inserter 131 has a generally T-bar construction. Handle 132 is in the form of a circular cylindrical cross bar attached to the proximal end of the shaft 136. Shaft 136 has a generally circular rod form. As illustrated in FIG. 3, an attachment formation 137 is provided at the distal end 134 of the shaft 136 and in the illustrated embodiment, may take the form of a screw thread. However, in other embodiments, the attachment formation may provide a push fit interface with a corresponding femur feature in the cement restrictor 150.

The stop 138 has a flared portion extending to a greater diameter than shaft 136 and provides an abutting shoulder portion 139. A circular cylindrical boss 152 extends toward the distal end and defines a groove or recess 154 therein. A C-clip or circlip 156 is located within circular groove 154. Circlip 156 is generally in the form of a C or split ring of a resilient material, such as a metal, for example stainless steel. The inserter part 131 of the cement restrictor inserter instrument illustrated in FIG. 3 may be made from a suitable metal or alloy, for example stainless steel.

Figures 4A, 4B, 4C, 4D, 4E:
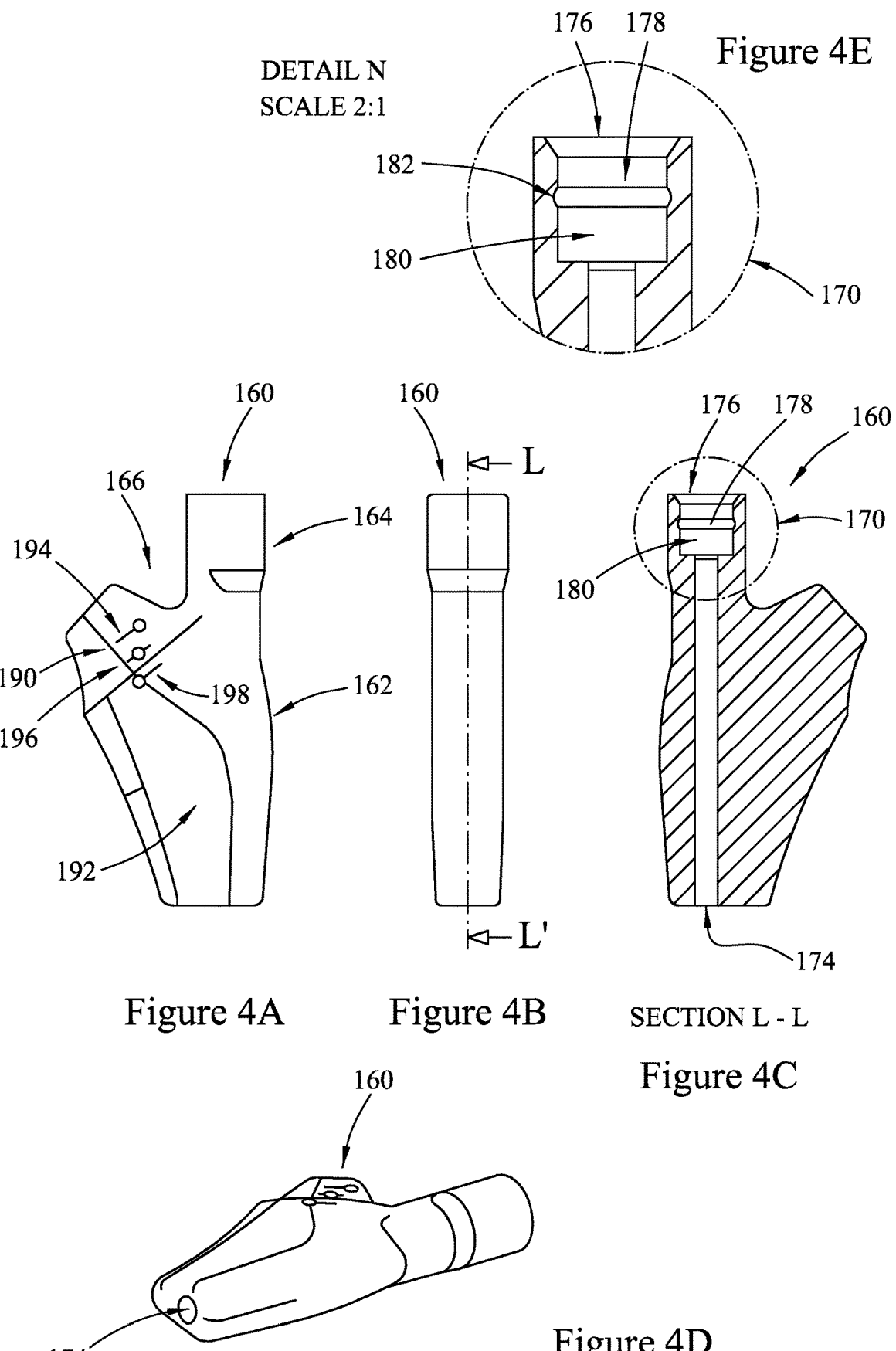
FIGS. 4A to 4E show various views and cross sectional views of a first embodiment of a body part of the instrument shown in FIG. 2.

FIGS. 4A to 4E show various views of a further body 160, generally similar to body 140 illustrated in FIG. 2. As explained in greater detail below, the major difference between the body 160 shown in FIGS. 4A to 4E and the body 140 shown in FIG. 2 is the length of the spacer element along a direction parallel to the axis of the shaft 136 of the inserter 131. FIG. 4A shows a side elevation of body 160 (generally in the anterior-posterior direction) and FIG. 4B shows a side elevation. FIG. 4C shows a cross-sectional view through the body along line L-L'. FIG. 4D shows a perspective view of the body 160 and FIG. 4E shows an expanded cross sectional view of a part 170 of the cross section of FIG. 4C.

As best illustrated in FIG. 4a, the body 160 generally has the same shape as the proximal part of the femoral stem 114 illustrated in FIG. 1. However, the body 160 corresponds to the proximal part only of the stem 114 and is distally truncated, in that that distal part of the prosthetic stem 114 is not present. Also the body 160 is truncated at the part corresponding to the neck 116 of the prosthetic stem 114. The part 162 of the body corresponding to the proximal part of the stem 114 may also have substantially the same dimensions as the proximal part of the stem 114. That is, the body 160 has generally the same shape and size as the proximal part of the corresponding prosthetic component 114.

It is not essential that the dimensions of the body and corresponding prosthesis are identical. The body may be a simplified versions of the proximal part of the stem which has generally the same form or shape and which would be easier and cheaper to machine.

Hence, generally speaking, the body should be as close in geometry as is economically reasonable to the corresponding prosthesis. However, the body should not be longer or wider or thicker than the final broach or trial or cutting instrument used to form the femoral cavity otherwise the body would contact the interior walls of the femoral cavity prematurely and prior to the cement restrictor having been inserted to the desired depth.

A spacer part 164 extends from a proximal part of the body 166 and generally along a longitudinal axis 168 of the body which is generally parallel to the longitudinal axis of the shaft 136 of the inserter 131. As best illustrated in FIG. 4C, the body 162 defines a channel 172 extending generally along the longitudinal axis and between a lower opening 174 and upper opening 176 of the spacer 164.

The spacer element 164 has a generally circular cylindrical construction and defines a slightly tapered cavity 178 therein. As best illustrated in FIGS. 4c and 4e, an inner wall 180 of the spacer defines a groove 182 therein extending around the longitudinal axis. Cavity 178 is sized to snugly received boss 152 therein and groove 182 is positioned and dimensioned to receive circuit 156 therein to provide a releasable attachment mechanism between the body 160 and remainder of the cement restrictor inserter 130.

Hence, the body 160 may be slid along shaft 136 of the inserter until the spacer 164 abuts the stop 138 to fix the position of the body relative to the remainder of the inserter. The releasable attachment mechanism prevents the body from being unintentionally removed from the shaft during handling.

As best illustrated in FIG. 4A, a visual depth guide feature 190 is provided on an anterior surface 192 of the body. A similar alignment feature is provided on the posterior side which is not visible in the Figures.

In the illustrated embodiment, the visual depth guide feature 190 is in the form of a plurality of markings 194, 196, 198, each comprising a linear section. The linear sections are arranged generally perpendicularly to the direction of the neck axis of the corresponding stem component 114. Indeed, corresponding markings 119 can be seen on the prosthetic stem component 114 in FIG. 1.

Figure 5:
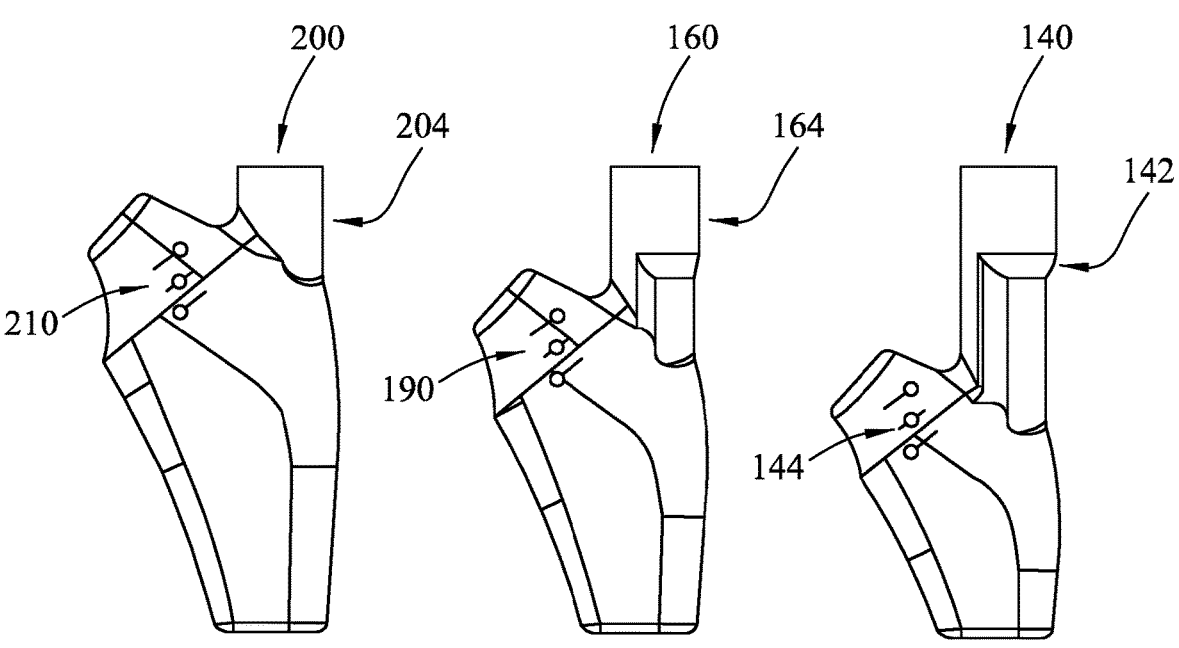
FIG. 5 shows side views of different sized body parts useable with the inserter shown in FIG. 3 and which may be provided as parts of a surgical instrument kit.

As described above, the body part 160, 140 of the inserter instrument 130 is releasably attachable to the inserter 131 by being slid along the shaft 136 and releasably attaching to the stop 138. In practice, a plurality of body parts each corresponding to a different size of prosthetic component may be provided. For example, FIG. 5 shows a first body 140, a second body 160 and a third body 200 each corresponding to a different sized prosthetic femoral stem. It will be appreciated that in other embodiments, a greater or lesser number of bodies may be provided. In this described example, the first body 140 corresponds to a smallest stem, the second body 160 corresponds to a medium sized stem and the third body 200 corresponds to a largest stem.

Generally speaking, the size of a stem is determined by its size in the medial-lateral direction. The length of the stem may also vary with the size of the stem such that a smaller stem will have a lesser length in the anterior-posterior direction than a larger sized stem. Therefore, the first body 140 corresponds to a prosthetic femoral stem having a smallest length in the inferior-superior direction, second body 160 corresponds to a second prosthetic femoral stem having a greater length in the inferior-superior direction than the first, and the third body 200 corresponds to a largest prosthetic femoral stem having a greatest length in the inferior-superior direction.

As the distance between the stop 138 and the distal end 134 of the inserter to which the cement restrictor is attached is fixed, the length of the spacer part of each body decreases as the size of the corresponding stem increases. In this way, the inserter 130 can be used to reliably position the cement restrictor 150 with the preferred separation from the distal-most point of the prosthetic implant by using the visual depth guide feature to be used to control the depth of insertion of the cement restrictor 150.

The first body 140 corresponds to a prosthetic stem with the shortest length in the inferior-superior direction and therefore has the longest spacer part 142 so as to position the visual depth guide features further down the shaft relative to the stop 138. The medium sized body 160 corresponds to a femoral stem having a greater length in the inferior-superior direction than the femoral stem corresponding to the first body 140 and therefore has a shorter spacer 164 so as to position the visual depth guide features 190 closer to the stop 138.

The third body 200 corresponds to a femoral stem having a greatest length in the inferior-superior direction and therefore has a shortest spacer 204 so as to position the visual depth guide feature 210 closest to the stop 138.

By varying the length of the spacer part along the longitudinal axis of the body, to compensate for the different lengths in the inferior-superior direction of the stems corresponding to the bodies, the visual depth guide features may be used to guide insertion of the cement restrictor 150 to a depth within the cavity corresponding to the desired separation 124 between the cement restrictor and the distal-most part of the prosthetic stem, when implanted.

With reference to FIG. 6 there is shown a flow chart illustrating a method 300 of using the cement restrictor inserter instrument 130 in order to insert a cement restrictor 150 at the appropriate depth within the intramedullary cavity of a femur. Various parts of the overall hip replacement procedure are omitted for the sake of clarity but are generally known to a person of ordinary skill in the art. Therefore, FIG. 6 illustrates merely those parts of the total hip replacement procedure useful to explaining the use of the inserter instrument 130. At 302, the femur is prepared. This may include resection of the native neck of the femur and also forming an intramedullary cavity extending generally along the proximal anatomical axis of the femur. Various cutting instruments such as brooches and rasps may be used to form the intramedullary cavity. In some embodiments, a trial femoral stem component which also functions as a final brooch may be used to form the cavity within the femur.

Figure 7:
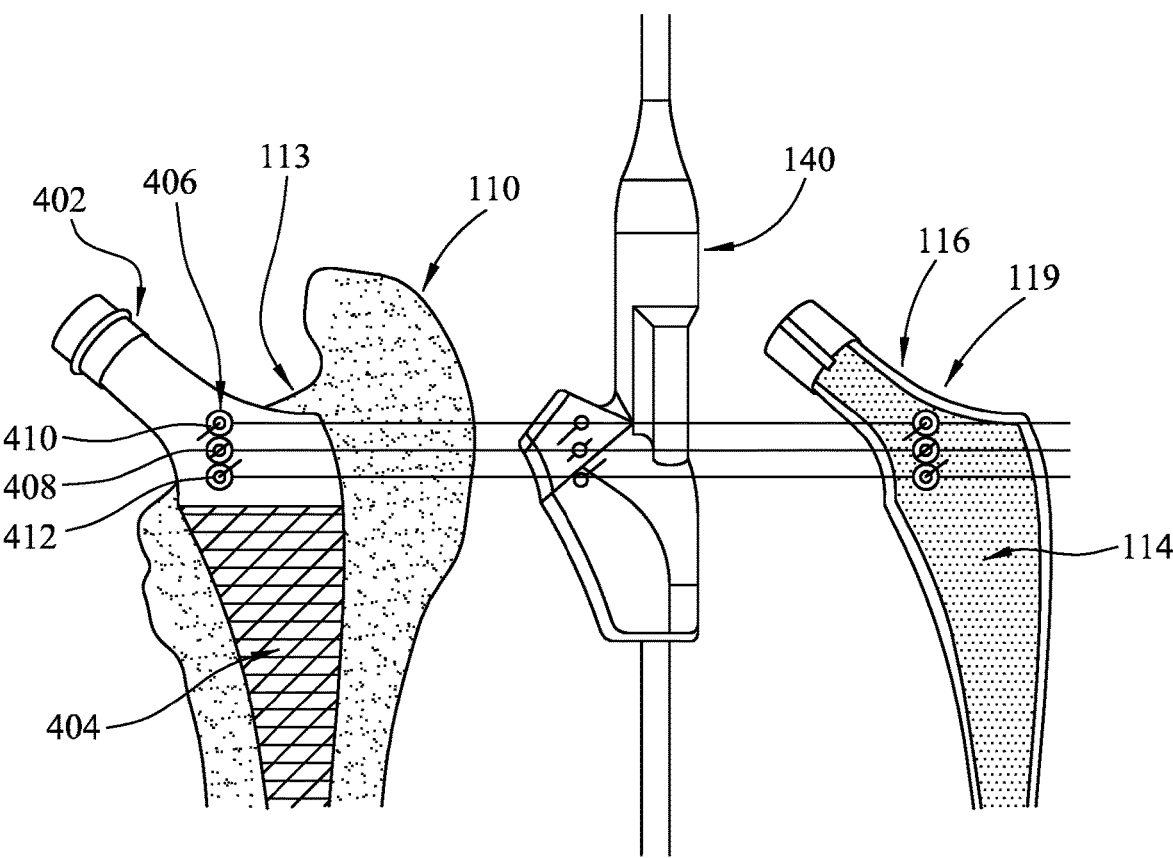
FIG. 7 illustrates the relationship between various trials, instruments and implants used during the method illustrated in FIG. 6.

For example, FIG. 7 shows a cross sectional view of a proximal part 110 of the patient's femur and shows the resection plane 113 resulting from resection of the native femoral neck. A trial femoral stem 400 is shown having a neck 402 and cutting teeth 404 disposed on the stem and which has been used to brooch the femoral cavity. An anterior side wall of the trial stem 400 includes a visual depth guide feature 406 similar to those present on the bodies, e.g. body 140 and the corresponding prosthetic femoral stem component 114. The visual depth guide feature 406 is similarly in the form of three parallel lines generally perpendicular to the neck axis of the stem. Each of the lines corresponds to a different amount of offset of the femur relative to the pelvis in the medial-lateral and inferior-superior directions. The middle line 408 may correspond to a neutral amount of medial-lateral offset and inferior-superior offset (also referred to leg length). The upper line 410 may correspond to a reduced amount of inferior-superior offset and medial-lateral offset. The lower line 412 may correspond to an increased amount of medial-lateral and inferior-superior offset. Hence, the surgeon may use trial stem 400 to complete broaching of the intramedullary cavity of the femur until a one of the markings corresponding to the desired change, if any, in the offset is aligned with the plane of the femoral resection. As illustrated in FIG. 7, the neutral offset line 408 is generally aligned with the resection plane 113 of the femur.

The femoral trial 400 has a correspondingly sized prosthetic femoral stem 114. However, the prosthetic femoral stem 114 has a slightly smaller size than the trial stem 400 in order to provide for the cement mantel 120 surrounding the prosthetic stem 114. Hence, once trialling has been completed at 304, the surgeon may determine the size of prosthetic femoral stem corresponding to the trial femoral stem 400.

As further illustrated in FIG. 7, body 140 has a shape and size corresponding to the prosthetic femoral stem 114. Hence at 306, the surgeon may select the body for the inserter corresponding to the selected size of the prosthetic femoral stem 114.

At 308, the selected body 104 may be attached to the inserter 131 by being slid along the shaft and attached via the releasable attachment mechanism. As discussed above, the position of the body 140 along the longitudinal axis of the inserter is determined by abutment of the spacer part 142 with the stop 138.

A cement restrictor trial may then be attached to the distal end of the inserter instrument 130 at 310. The inserter instrument 130 may then be used to introduce the cement restrictor trial into the intramedullary cavity of the femur. Generally, the purpose of the cement restrictor trial is to gauge the appropriate diameter of the cement restrictor to be used. Hence, the surgeon may move the cement restrictor trial distally into the intramedullary cavity in order to gauge the diameter of the intramedullary cavity near the intended target position of the cement restrictor. As the exact positioning of the trial is not essential, this may be simply done by feel. Alternatively, or additionally, at 312, the surgeon may use the visual depth guide feature 144 on the anterior surface of the body by comparing the position of the marking corresponding to the previously planned position, e.g. marking 408, relative to the resection plane 113 of the femur.

At 314, the surgeon may determine whether the cement restrictor trial has the appropriate diameter for the target insertion depth. If not, then the method may return, as illustrated by flow line 316 back to step 310 and a different cement restrictor trial may be attached to the distal end of the introducer of a greater or lesser diameter. Hence, the method may repeat until a diameter of the cement restrictor has been successfully determined.

At 318, a cement restrictor having the diameter determined from the trialling is releasably attached to the distal end of the rod, after having removed the cement restrictor trial. In embodiments in which a threaded connection is used, then the cement restrictor is screwed on to the screw formation at the distal end 134 of the inserter instrument 130. In other embodiments, in which a push fit attachment mechanism is used, then the cement restrictor 150 may simply be pushed on to the distal end 134 of the inserter instrument 130. Then at 320, the cement restrictor 150 is introduced into the intramedullary cavity and the inserter 130 is used to insert the cement restrictor 150 into the intramedullary cavity. The shape of the body 140 helps to ensure that the longitudinal axis of the inserter 130 is generally aligned with central axis of the cavity rather than being tilted in the coronal plane. However, the dimensions of the body 140 are smaller than the dimensions of the trial stem 400 and therefore do not themselves limit the insertion depth of the cement restrictor. Rather, the shape of the body helps to provide visual context to the surgeon as to the correct depth of insertion of the cement restrictor. In particular, the visual depth guide features on the body 140 correspond to visual depth guide features 406 on the trial stem and also the visual depth guide features 119 on the prosthetic stem.

Hence, the surgeon may progress the inserter instrument into the intramedullary canal until the marking corresponding to the previously trialled marking, the central line in this example, is aligned with the resection plane 113 of a femur. The surgeon may now be confident that the cement restrictor 150 has been positioned at a target depth within the intramedullary canal of the femur which will have the appropriate degree of separation 124 from the distalmost part of the prosthetic stem 114 when inserted in the intramedullary canal at the corresponding position, as defined by the same middle line of the visual depth guide features 119 being aligned with the resection plane 113.

Hence, in embodiments in which a push-fit is used, the greater frictional force between the inner walls of the femur and the outer surface of the cement restrictor will overcome the frictional force of the push-fit interface between the distal end of the inserter and the cement restrictor and so the inserter instrument 130 may simply be withdrawn from the intramedullary cavity leaving the cement restrictor 150 secured in place at the target depth.

Alternatively, if a screw threaded attachment is used, then the handle 132 may be used to rotate the shaft 136 which may rotate relative to the body 140 thereby allowing the distal end 134 of the inserter to be detached from the cement restrictor 150. The circlip and groove releasable attachment mechanism permits rotation of the shaft 136 relative to the body thereby permitting disengagement of the screw thread attachment mechanism.

Hence, at 322, the inserter is detached from the cement restrictor, which is left in place at the target depth, as illustrated in FIG. 1.

Consequently, cement may be introduced into the intramedullary canal and then the prosthetic stem 114 introduced and positioned with the central markings of its corresponding visual depth guide features aligned with the resection plane 113 of the femur.

With reference to FIGS. 8A and 8B there are shown side and perspective views of a further embodiment of a body 500 which may be used as part of the cement restrictor inserter instrument. Body 500 is generally similar to the first embodiment described above other than the releasable attachment mechanism by which the body is releasably attached to the stop of the inserter. The body 500 shown in FIGS. 8A and 8B has generally the same geometry and size as the body 140 shown in FIGS. 2, 5 and 7. The body 500 generally has a shape and size corresponding to the proximal part of a corresponding femoral stem 114. A visual depth guide feature 502 in the form of a plurality of markings each including a line is provided on an anterior surface 504 of the body 500.

Similarly, a spacer 506 extends from a superior part of body 500 generally along the longitudinal axis of the body and defines a circular cylindrical cavity therein for receiving the shaft 136 of the inserter 131 in use. A proximal end of spacer 506 defines a shoulder 508 arranged to abut against the stop 138 of the inserter. However, in the illustrated embodiment, instead of using a circlip and groove, the releasable attachment mechanism 510 is in the form of a snap fit connector including four resilient tongues. The stop 138 of the inserter 131 defines a generally annular cavity therein and also a groove within an inner wall of the spacer configured to receive the protrusions at the free ends of the tongue, e.g. protrusion 512 of tongue 514. Hence, body 500 can be used generally similarly to the first embodiment described above. Again, the snap fit piece of attachment mechanism allows the shaft of the inserter to rotate relative to the body and therefore the cement restrictor inserter provided using this body can be used with cement restrictors attached via a push fit or screw fit connection.

FIGS. 9A and 9B show side and perspective views of a third embodiment of a body 600. Again, body 600 has the shape and dimensions of a corresponding prosthetic femoral stem 114 and include a visual depth guide feature 602 on an anterior surface 604 thereof. In the illustrated embodiment, the visual depth guide feature 602 is in the form of a plurality of circles or dots equally spaced along an axis parallel to the longitudinal axis of the body 600. Body 600 generally corresponds to body 200 and similarly includes a spacer element 606 extending from a superior end of body 600. A proximal surface 608 of spacer 606 is arranged to abut the stop 138 of the inserter to control the position of the body relative to the inserter instrument.

However, as best illustrated in FIG. 9B, the releasable attachment mechanism of the body 600 is provided by a generally open channel 610 being defined by portions of the anterior 604 and posterior 612 surfaces of the body. The channel 610 extends generally along the longitudinal axis of the body and is dimensioned to receive the shaft 136 of the inserter 131 immediately below the stop 138. When using this body, the inserter 131 omits boss 152 such that the body 600 may simply be clipped onto the shaft 136 of the inserter with the spacer 606 abutting the distalmost surface of the stop 138. The body 600 is made from a suitable plastic material in order to provide a snap fit releasable attachment mechanism. As also illustrated in FIG. 9b, a groove 614 may be defined by an inner surface wall 616 of the channel 610. A proud ring may extend around the shaft 136 of the inserter 131 and positioned to be received within groove 614 when surface 608 abuts the distal surface of stop 138 to ensure correct relative positioning of the body 600 relative to the stop 138 and prevent the body from being slid distally down the shaft 136 into an incorrect relative position. The ring of material may be an integral part of the shaft having been formed by machining rather than being some separate part subsequently attached to the shaft It will be appreciated that the use of cement restrictors is not limited to femoral stems and indeed may be used for other cemented orthopaedic implants having some stem like portion which extends into a cavity and which is not visible to a surgeon. The use of a body having the same shape and dimensions as a proximal part of the corresponding prosthetic implant is intended to help the surgeon to better understand and/or recollect whether the cement restrictor insertion depth is correct by using some visual depth guide feature to be compared with some part of the patient's bone but within the common context of the body and corresponding prosthetic implant. In many embodiments, the body is not itself used to control the depth of insertion. Rather, the body will have smaller dimensions than the cavity owing to the gap required between the walls of the cavity and the prosthetic implant to receive the cement cavity. The body may help with some centralisation of the inserter by partially filling the proximal part of the cavity. However, the shape and size of the body is more intended to provide visual and contextual feedback to the surgeon so that they can immediately understand that the body is at the correct position as the implant will be at that same position.

The relative position of the cement restrictor for the currently select body size is taken care of by the correct positioning of the body on the rod owing to the length of the spacer element and the position of the visual depth guide features on the body along an axis generally parallel to the longitudinal axis of the shaft of the inserter. Hence, the same inserter shaft can be used with multiple different bodies corresponding to different sized prosthetic implants with different sized stem lengths.

Therefore one aspect of the disclosure also relates to a kit of parts or surgical system including the inserter instrument, multiple bodies of different sizes and optionally multiple corresponding prosthetic implants of different sizes.

Other common orthopaedic implants which may use cemented stems, include humeral stems, both conventional and reverse shoulder, and also the tibial component and the femoral component of a knee prosthesis. Some femoral components include a cemented stem, especially those used in revision surgery.

For example, a body 650 having the shape and size of a corresponding prosthetic tibial component is illustrated in FIGS. 10A and 10B. The prosthetic tibial component may generally have the form of a tibial tray with a stem extending from an inferior surface and providing an attachment mechanism for a bearing surface on a superior side. Hence, when a tibial tray with a cemented stem is being used, then the same general approach may also be used in which the body 650 has the shape and dimension of a proximal part of the tibial prosthesis, i.e. not including at least the distalmost portion of the stem. For example, as illustrated in FIGS. 10A and 10B, the body 650 includes a tibial tray part 652 having the general shape and size of the tibial tray of the corresponding prosthetic component. At least a part of a tibial stem 654 extends in an inferior direction from an inferior side 656 of the tibial tray part 652. A pair of wings or flanges 658, 660 extend between the stem 654 and the inferior side 656 of the tray 652. Similarly to the bodies described above, a spacer 662 extends from a superior surface 664 of the tray 652 generally in the direction of the inferior-superior axis and parallel to the longitudinal axis of the shaft 136 of the inserter 131. The spacer 662, tray part 652 and stem part 654 between them define a central circular cylindrical cavity 666 within which the shaft 136 of the inserter 131 is inserted in use. An inner surface 668 of the spacer 662 defines a groove 670 arranged to receive the circlip of the inserter 131 to provide a releasable attachment mechanism which also permits rotation of the shaft 136 relative to the body 650.

The length of the spacer 662 in the direction of the longitudinal axis of the shaft 136 is selected such that when the free end of the spacer 662 abuts the stop 138 when mounted on the inserter 131, the cement restrictor would be located at the appropriate distance 124, within the tibial intramedullary cavity, from the distal most part of the stem of the corresponding prosthetic component when the underside or inferior surface 656 of the tray 652 is seated on the resected surface of the tibia (resulting from the proximal tibial cut). Hence, in this embodiment correct positioning of the cement restrictor is determined by the surgeon observing that the tibial tray part 652 is seated flush on the resected tibial surface, rather than comparing a marking on, or structural part of, the body with some part of the bone of the patient. Hence, in this embodiment, the under surface or inferior surface 656 of the tray part 652 provide the visual depth guide feature of the body 650 by which the insertion depth of the cement restrictor may be visually assessed by the surgeon.

By way of further example, FIG. 11 shows a further embodiment of a cement restrictor inserter instrument 700 including a body 710 generally having the shape and dimensions of a humeral stem or shoulder stem prosthesis. The shoulder stem prosthesis is typically used in a reverse shoulder arthroplasty procedure. The shoulder stem prosthesis is inserted in an intramedullary cavity within the humerus of the patient to provide a shallow cup into which a bearing component may be inserted to provide an articulating surface for a corresponding ball type prosthetic implant located within the shoulder of the patient. Hence, body 710 generally has the shape and form of the humeral prosthetic implant including a part of the stem 712 and a cup like portion 714. The cup portion 714 includes a generally annular wall 716 an upper edge or surface 718 of which provides the visual depth guide feature used to assess correct positioning of the cement restrictor inserter within the intramedullary cavity of the humerus. Similarly, a spacer part 720 extends from a superior part of the body 710 with a groove 722 defined within an interior surface 724 of the spacer part 720 therein for releasably attaching the body 710 to the circlip of the inserter 131. The spacer 720, cup part 714 and stem part 712 between them define a central circular cylindrical cavity 726 within which the shaft 136 of the inserter 131 is inserted in use.

The length of the spacer 720 in the direction of the longitudinal axis of the shaft 136 is selected such that when the free end of the spacer 720 abuts the stop 138 when mounted on the inserter 131, the cement restrictor would be located at the appropriate distance 124, within the humeral intramedullary cavity, from the distal most part of the stem of the corresponding prosthetic component when the surface 718 of the wall 716 is aligned with the rim of the cavity formed in the proximal part of the humerus. Use of the cement restrictor inserter instrument 700 illustrated in FIG. 11 is generally similar to that described above with reference to FIG. 2 other than the correct depth of insertion of the cement restrictor 150 being determined by the edge or surface 718 of the body being aligned with a resected or otherwise prepared part of the humerus of the patient.

The body parts described above may be made from various materials and various plastics, especially polymeric plastics, are particularly suitable. For example, the body part may be made from Acetal or Polyoxymethylene (POM), Polyphenylsulphone (PPS), Polyetheretherketone (PEEK), Polyaryletherketone (PAEK) or similar and also filled versions of those plastics or similar.

Hence, it would be apparent that there are a number of different benefits provided by the various sets of instrumentation described herein and methods enabled thereby.

In this specification, example embodiments have been presented in terms of a selected set of details. However, a person of ordinary skill in the art would understand that many other example embodiments may be practiced which include a different selected set of these details. It is intended that the following claims cover all possible example embodiments.

The flowchart steps in the above Figures may be executed in other orders, unless a specific order is inherently required or explicitly stated. Also, those skilled in the art will recognize that while one example methods have been discussed, the material in this specification can be combined in a variety of ways to yield other examples as well, and are to be understood within a context provided by this detailed description.

While the disclosure is amenable to various modifications and alternative forms, specifics thereof have been shown by way of example in the drawings and described in detail. It should be understood, however, that other embodiments, beyond the particular embodiments described, are possible as well. All modifications, equivalents, and alternative embodiments falling within the scope of the appended claims are also envisaged.

The invention claimed is:

1. A cement restrictor inserter instrument comprising:
an inserter having a handle at a proximal end, a cement restrictor attachment formation at a distal end for releasably attaching a cement restrictor, a shaft extending from the proximal end to the distal end and a stop on the shaft and between the proximal end and the distal end; and
a body having a shape corresponding to the shape of an orthopaedic prosthetic implant, a spacer, a visible depth guide feature and a releasable attachment mechanism by which the body is releasably attachable to the a rod, and wherein the spacer is configured to position the visible depth guide feature at a fixed position relative to the inserter when the spacer abuts the stop corresponding to a target cement restrictor position when the visible depth guide feature is aligned with a feature of a bone of a patient in which the cement restrictor is to be inserted.

2. The cement restrictor inserter instrument as claimed in claim 1, wherein the releasable attachment mechanism includes a push fit or snap fit mechanism.

3. The cement restrictor inserter instrument as claimed in claim 1, wherein the stop includes an attachment formation and wherein the releasable attachment mechanism interacts with the attachment formation.

4. The cement restrictor inserter instrument as claimed in claim 3, wherein the attachment formation includes a circlip within a part of the stop and the releasable attachment mechanism of the body includes a groove arranged to receive the circlip.

5. The cement restrictor inserter instrument as claimed in claim 1, wherein the body defines an open channel or a closed channel extending along a longitudinal axis of the body and configured to accept the shaft.

6. The cement restrictor inserter instrument as claimed in claim 1, wherein the releasable attachment mechanism permits rotation of the shaft relative to the body.

7. The cement restrictor inserter instrument as claimed in claim 1, wherein the cement restrictor attachment formation comprises a push fit formation.

8. The cement restrictor inserter instrument as claimed in claim 1, wherein the cement restrictor attachment formation comprises a screw thread.

9. The cement restrictor inserter instrument as claimed in claim 1, wherein the visible depth guide feature comprises a surface or an edge of a part of the body.

10. The cement restrictor inserter instrument as claimed in claim 1, wherein the visible depth guide feature comprises a marking on a surface of a part of the body.

11. The cement restrictor inserter instrument as claimed in claim 1, wherein the orthopaedic prosthetic implant is a humeral stem, a femoral stem, femoral component of a knee or a tibial component.

12. The cement restrictor inserter instrument as claimed in claim 1, wherein the body has a size corresponding to the size of the orthopaedic prosthetic implant.

13. A kit of surgical instrument parts comprising:
a cement restrictor inserter instrument comprising:
an inserter having a handle at a proximal end, a cement restrictor attachment formation at a distal end for releasably attaching a cement restrictor, a shaft extending from the proximal end to the distal end and a stop on the shaft and between the proximal end and the distal end; and
a body having a shape corresponding to the shape of an orthopaedic prosthetic implant, a spacer, a visible depth guide feature and a releasable attachment mechanism by which the body is releasably attachable to a rod, and wherein the spacer is configured to position the visible depth guide feature at a fixed position relative to the inserter when the spacer abuts the stop corresponding to a target cement restrictor position when the visible depth guide feature is aligned with a feature of a bone of a patient in which the cement restrictor is to be inserted; and
a further body having a shape corresponding to the shape of the orthopaedic prosthetic implant, a further spacer, a further visible depth guide feature and a further releasable attachment mechanism by which the further body is releasably attachable to the shaft, and wherein the further body has a different size to the body and corresponds to the shape of a different size of the orthopaedic prosthetic implant and wherein the further spacer has a different size to the spacer and is configured to position the further visible depth guide feature at a different fixed position relative to the inserter when the further spacer abuts the stop corresponding to the target cement restrictor position when the further visible depth guide feature is aligned with the feature of the bone of the patient in which the cement restrictor is to be inserted.

* * * * *